United States Patent [19]

Subramanian

[11] Patent Number: 6,166,273
[45] Date of Patent: Dec. 26, 2000

[54] PROCESSES FOR FLUORINATING AROMATIC RING COMPOUNDS

[75] Inventor: Munirpallam A. Subramanian, Kennett Square, Pa.

[73] Assignee: E.I. du Pont de Nemours and Company, Wilmington, Del.

[21] Appl. No.: 09/360,958

[22] Filed: Jul. 27, 1999

Related U.S. Application Data

[60] Provisional application No. 60/094,388, Jul. 28, 1998.

[51] Int. Cl.[7] .......................... C07C 25/13; C07C 69/76; C07C 63/04; C07C 255/00; C07C 233/00
[52] U.S. Cl. ..................... 570/147; 570/144; 560/103; 562/493; 558/411; 564/183; 564/442; 568/656; 568/716; 568/433; 546/345
[58] Field of Search ................................. 570/147, 144; 560/103; 562/493; 558/411; 564/183, 442; 568/656, 716, 433; 546/345

[56] References Cited

U.S. PATENT DOCUMENTS

| | | |
|---|---|---|
| 2,892,000 | 6/1959 | Skiles . |
| 3,398,203 | 8/1968 | Olson . |
| 4,394,527 | 7/1983 | Fischer et al. . |
| 4,978,649 | 12/1990 | Surovikin et al. . |
| 5,756,834 | 5/1998 | Pasenok et al. . |

FOREIGN PATENT DOCUMENTS

| | | |
|---|---|---|
| 52-122310 | 10/1977 | Japan . |
| WO 97/30932 | 8/1997 | WIPO . |

OTHER PUBLICATIONS

R.G. Plevey et al., Fluorination with Complex Metal Fluorides Part. II, *Journal of Fluorine Chemistry*, 3, 259–266, 1973.

*Primary Examiner*—Alan Siegel

[57] ABSTRACT

A process is provided for increasing the fluorine content of benzene or pyridine rings which are optionally substituted with from 1 to 3 inert substituents. The process involves (a) contacting the ring with a metal fluoride composition comprising cupric fluoride ($CuF_2$) at a temperature above 250° C. sufficient to transfer F from cupric fluoride to the optionally substituted ring, thereby chemically reducing the metal fluoride composition; (b) oxidizing the reduced metal fluoride composition from (a) in the presence of HF to regenerate a metal fluoride composition comprising cupric fluoride; and (c) employing regenerated metal fluoride composition of (b) in (a).

1 Claim, No Drawings

PROCESSES FOR FLUORINATING AROMATIC RING COMPOUNDS

This application claims the priority benefit of U.S. Provisional Application 60/094,388, filed Jul. 28, 1998.

FIELD OF THE INVENTION

This invention relates to a process for increasing the fluorine content of a benzene or pyridine ring using copper fluoride.

BACKGROUND

Fluorobenzene, an agricultural chemicals intermediate, is typically produced by the reaction of aniline and sodium nitrite in the presence of hydrogen fluoride. A diazonium salt intermediate is formed during this process which because of its instability adds to the cost of manufacture. U.S. Pat. No. 4,394,527 discloses a process for monofluorinating a benzene nucleus comprising reacting a benzene compound in the liquid phase with argentic fluoride which is reduced to argentous fluoride during the reaction.

There is still a need for an efficient commercial processes for preparing fluorobenzene or, more generally, fluorinating compounds having a benzene nucleus using less expensive materials.

SUMMARY OF THE INVENTION

A process is provided for increasing the fluorine content of an aromatic ring selected from the group consisting of a benzene ring, a pyridine ring, a benzene ring substituted with from 1 to 3 inert substituents and a pyridine ring substituted with from 1 to 3 inert substituents. The process comprises (a) contacting the aromatic ring with a metal fluoride composition comprising cupric fluoride ($CuF_2$) at a temperature above 250° C. sufficient to transfer F from cupric fluoride to the aromatic ring, thereby chemically reducing the metal fluoride composition; (b) oxidizing the reduced metal fluoride composition from (a) in the presence of HF to regenerate a metal fluoride composition comprising cupric fluoride; and (c) employing regenerated metal fluoride composition of (b) in (a).

DETAILED DESCRIPTION

In one embodiment of this invention the regenerable reagent, cupric fluoride ($CuF_2$), is reacted with unsubstituted benzene to produce fluorobenzene. Benzene may be passed over cupric fluoride at reaction conditions until an economically insufficient amount of fluorobenzene is recovered. This reaction is shown schematically in equation 1.

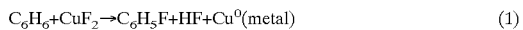

$$C_6H_6+CuF_2 \rightarrow C_6H_5F+HF+Cu^0(metal) \quad (1)$$

The hydrogen fluoride can be used to regenerate cupric fluoride from the copper metal as shown in equation 2.

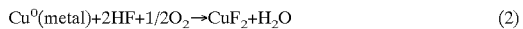

$$Cu^0(metal)+2HF+1/2O_2 \rightarrow CuF_2+H_2O \quad (2)$$

The copper metal is typically reacted with HF and oxygen at a temperature of from about 250° C. to about 700° C., preferably from about 375° C. to about 425° C. Pure oxygen, air or oxygen diluted with inert gases such as nitrogen or argon may be used along with the HF. The regeneration reaction is normally done at atmospheric pressure or slightly above atmospheric pressure for about 1 to about 24 hours. The reaction variables such as time, temperature and oxygen flow can be balanced one against the other to optimize the reaction of copper to copper fluoride. For example, as the air flow and temperature are increased, the reaction time is decreased. The regenerated metal fluoride composition may then be recycled for contact with additional benzene.

In another embodiment of this invention a mixture of benzene, HF and oxygen are contacted with the metal fluoride composition comprising cupric fluoride at reaction conditions. The overall reaction is shown schematically in equation 3.

$$C_6H_6+HF+1/2O_2 \rightarrow C_6H_5F+H_2O \quad (3)$$

This embodiment may be viewed as at least partially regenerating the metal fluoride composition in situ.

The contacting of benzene with cupric fluoride ($CuF_2$), HF and oxygen in the vapor phase is done at a temperature of at least about 250° C. The reaction pressure can be subatmospheric, atmospheric or superatmospheric; generally near atmospheric pressures are preferred.

The contact time is typically from about 1 to about 120 seconds (e.g., from about 5 to 60 seconds).

The reaction can also be done in the presence of inert gases which are stable under the reaction conditions such as nitrogen and argon.

Unreacted benzene can be recycled to the reactor for the production of additional fluorobenzene. The fluorobenzene may be recovered from the reaction product and any unreacted benzene by conventional procedures such as distillation.

Unsupported cupric fluoride may be used as the metal fluoride composition. Supported cupric fluoride may also be used. Suitable supports include those selected from the group consisting of fluorided alumina, fluorided magnesia, fluorided calcia and oxidatively stable carbon.

By fluorided alumina is meant a composition comprising aluminum, oxygen and fluorine. The fluoride content of the fluorided alumina can vary over a wide range, from about 0.001% to about 67.9% by weight. By fluorided magnesia is meant a composition comprising magnesium, oxygen and fluorine. The fluoride content of the fluorided magnesia can vary over a wide range, from about 0.001% to about 61.0% by weight. By fluorided calcia is meant a composition comprising calcium, oxygen and fluorine. The fluoride content of the fluorided calcia can vary over a wide range, from about 0.001% to about 48.7% by weight.

Oxidatively stable carbons are described in International Publication Number WO 97/30932. Particularly preferred carbons include three dimensional matrix porous carbonaceous materials. Examples are those described in U.S. Pat. No. 4,978,649, which is hereby incorporated by reference herein in its entirety. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon—carbon composite material is thus formed.

While the above description has been provided in the context of benzene fluorination, it will be recognized that the procedure can also be used to fluorinate pyridine or to fluorinate benzene or pyridine which is partially substituted with inert substituents (i.e., substituents which are inert under the conditions of the fluorination). Reference is made to U.S. Pat. No. 5,756,834 for representative substituents (chlorine excepted) considered inert under fluorination conditions. Example substituents include F, $CF_3$, COOH, COOR, $CONH_2$, $CONR^1R^2$, CN, CHO, $NO_2$, $NH_2$, $OCH_3$, $OCF_3$, $OCCl_3$, OH and $CCl_3$, where R, $R^1$ and $R^2$ are independently selected from $C_1$ to $C_6$ linear or branched alkyl groups. Examples of substituted benzenes suitable for fluorination are fluorobenzene and trifluoromethylbenzene. Examples of substituted pyridines suitable for fluorination are fluoropyridines and trifluoromethylpryidines.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

Example 1

Preparation of Fluorobenzene

An Inconel® nickel alloy tube reactor was packed with cupric fluoride ($CuF_2$, 5 g). The catalyst was heated to reaction temperature under a nitrogen flow. The nitrogen flow was adjusted to 20 cc/min. and benzene was then passed through a vaporizer over the catalyst at a 2 mL/hour flowrate. Reaction products were analyzed using a Hewlett Packard 6890 Gas Chromatograph/5973Mass Spectrometer. All analyses are reported in area % and are shown in Table 1.

The conversion decreased with time due to the formation of copper metal. Microscopic examination of the partially spent $CuF_2$ showed the formation of copper metal on the surface of the particles.

TABLE 1

| T (° C.) | % $C_6H_5F$ |
|---|---|
| 450 | 6.3 |
| 475 | 9.4 |
| 550 | 15 |

Example 2

In this example, $CuF_2$ was reacted with benzene under the same conditions as used in Example 1 to form fluorobenzene. At the end of the reaction all the $CuF_2$ was converted to copper metal. The copper metal formed was left in the reactor and treated with anhydrous HF and $O_2$ for 6 hours at 400° C. X-ray analysis of the product showed the formation of $CuF_2$. The regenerated $CuF_2$ was again reacted with benzene to form fluorobenzene. For the same amount of $N_2$/benzene flow through the reactor, it was noted that the conversion of fluorobenzene at 550° C. was about 30% for a single-pass, which is nearly twice that of the previous run.

What is claimed is:

1. A process for increasing the fluorine content of an aromatic ring selected from the group consisting of a benzene ring, a pyridine ring, a benzene ring substituted with from 1 to 3 inert substituents, and a pyridine ring substituted with from 1 to 3 inert substituents, comprising:

(a) contacting the aromatic ring with a metal fluoride composition comprising cupric fluoride at a temperature above 250° C. sufficient to transfer F from cupric fluoride to the aromatic ring, thereby chemically reducing the metal fluoride composition;

(b) oxidizing the reduced metal fluoride composition from (a) in the presence of HF to regenerate a metal fluoride composition comprising cupric fluoride; and (c) employing regenerated metal fluoride composition of (b) in (a).

* * * * *